(12) United States Patent
Carey-Hench

(10) Patent No.: US 9,895,486 B1
(45) Date of Patent: Feb. 20, 2018

(54) DEVICE FOR SECURING LOOSE TUBING OR WIRES TO CLOTHING

(71) Applicant: Ruth Carey-Hench, New Holland, PA (US)

(72) Inventor: Ruth Carey-Hench, New Holland, PA (US)

( * ) Notice: Subject to any disclaimer, the term of this patent is extended or adjusted under 35 U.S.C. 154(b) by 0 days.

(21) Appl. No.: 15/241,499

(22) Filed: Aug. 19, 2016

(51) Int. Cl.
*A61M 5/14* (2006.01)
*A61M 39/08* (2006.01)
*A61M 27/00* (2006.01)
*A61M 16/00* (2006.01)

(52) U.S. Cl.
CPC ...... *A61M 5/1418* (2013.01); *A61M 16/0003* (2014.02); *A61M 27/00* (2013.01); *A61M 39/08* (2013.01)

(58) Field of Classification Search
CPC ............ A61M 5/1418; A61M 16/0003; A61M 27/00; A61M 39/08; Y10T 24/1394; Y10T 24/45796; Y10T 24/45812
See application file for complete search history.

(56) References Cited

U.S. PATENT DOCUMENTS

| 3,896,527 A * | 7/1975 | Miller | A44B 99/00 16/DIG. 13 |
| 4,707,906 A * | 11/1987 | Posey | A61G 7/0503 128/DIG. 26 |
| 5,507,460 A * | 4/1996 | Schneider | A61M 5/1418 24/601.2 |
| 5,669,118 A * | 9/1997 | Frano | A44B 11/04 24/198 |
| 2008/0047114 A1* | 2/2008 | Wu | A44B 11/2584 24/700 |

\* cited by examiner

*Primary Examiner* — Robert Sandy
(74) *Attorney, Agent, or Firm* — Miller Law Group, PLLC

(57) ABSTRACT

A device for securing tubing or wiring to an article of clothing can be formed from plastic by injection molding. The device includes a primary body portion formed with a shaped opening therein. The shaped opening has an enlarged circular part and an integral linear part. The device also includes a closure button formed with a narrow neck attached to a support member, which in turn is connected to the primary body portion by a tether. The button is sized to fit through the circular opening so that the neck can slide into the linear part and trap an article of clothing between the closure member and the primary body portion. The primary body portion is also formed with a pair of clips that are appropriately sized to receive tubing, such as IV tubing, that can be supported on the patient's clothing and facilitate mobility for the patient.

19 Claims, 6 Drawing Sheets

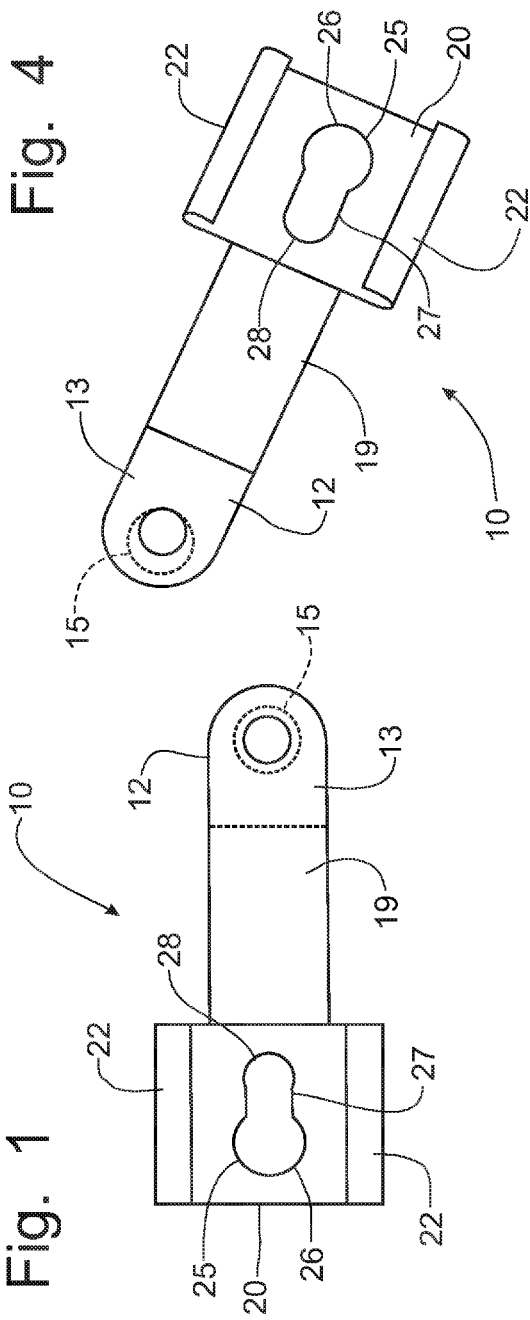

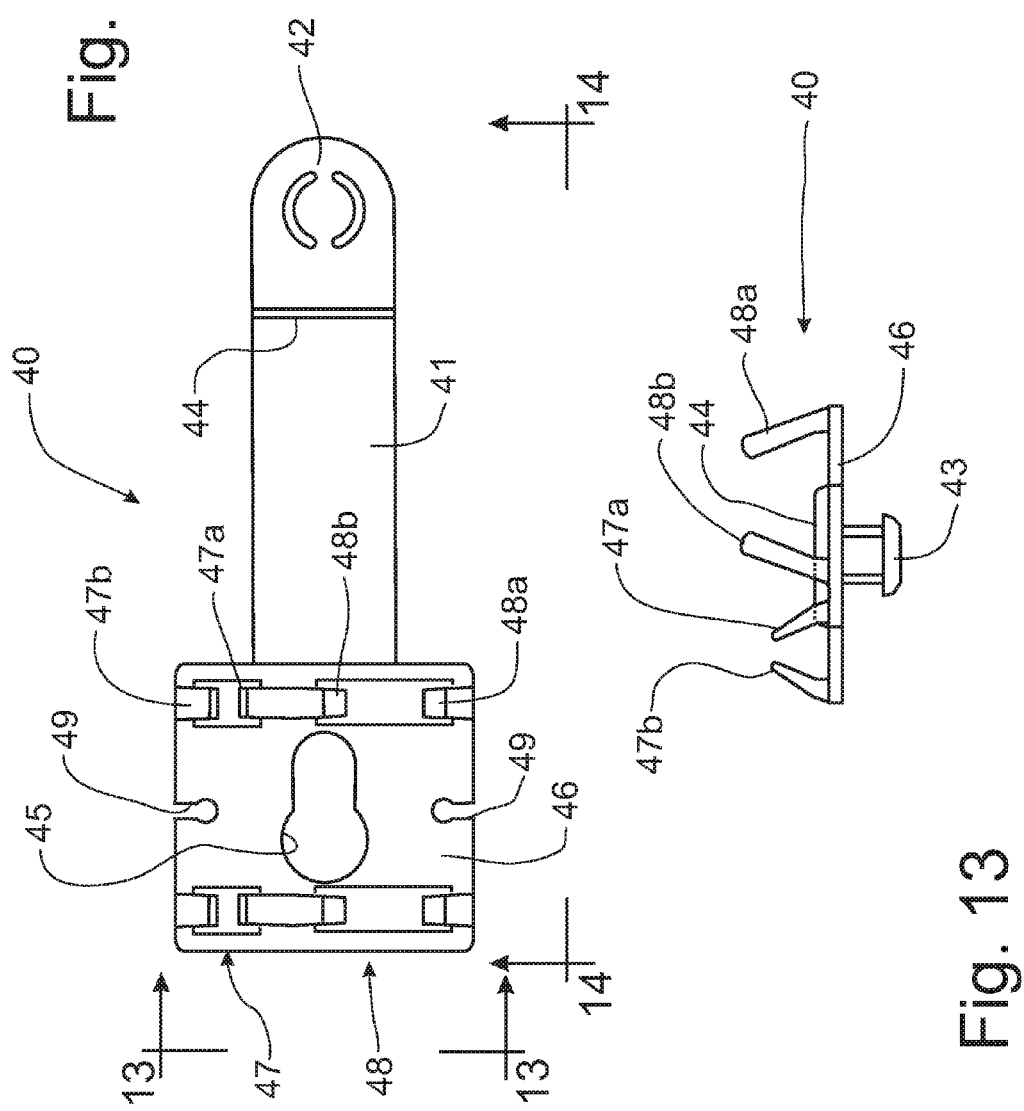

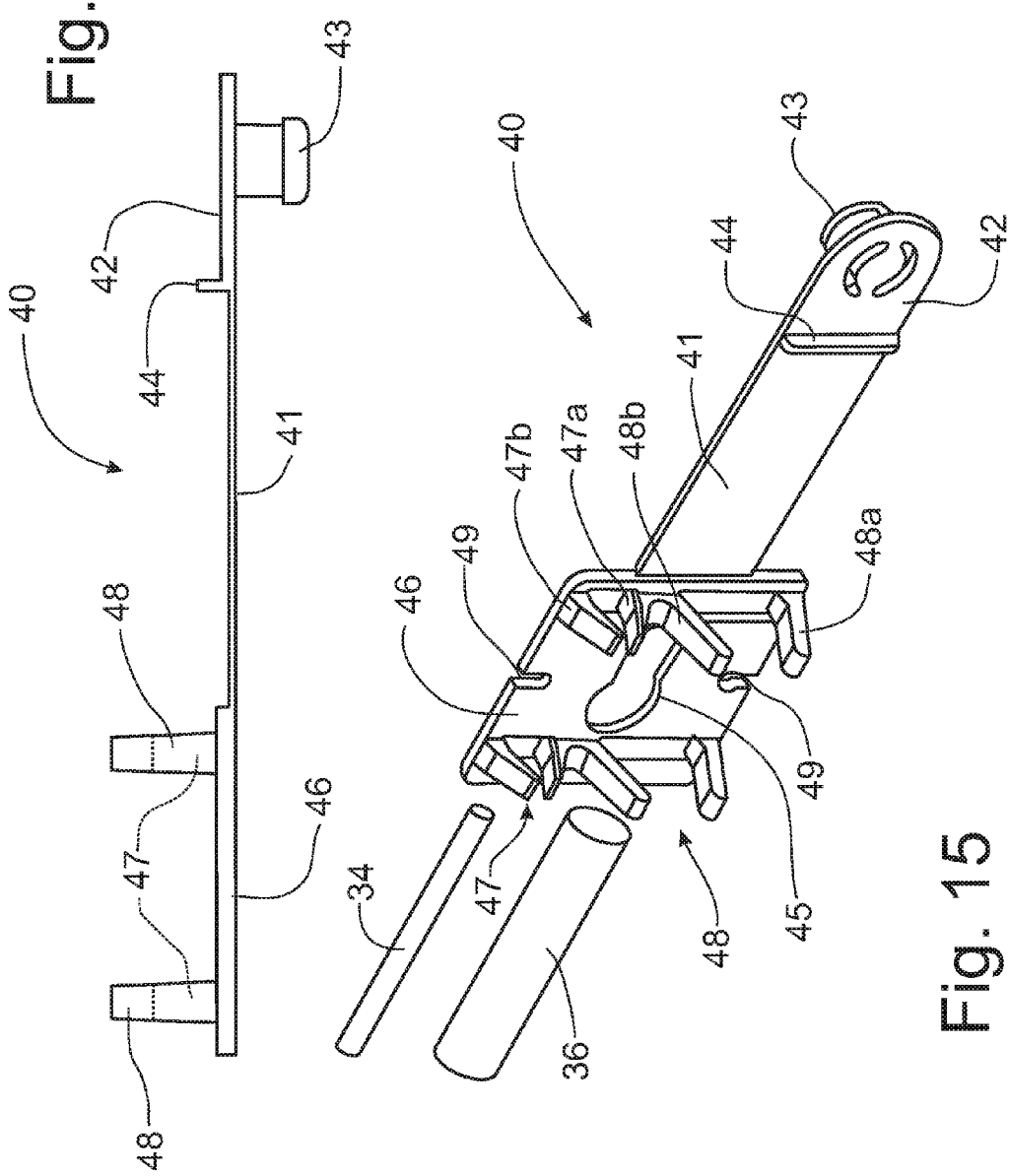

DEVICE FOR SECURING LOOSE TUBING OR WIRES TO CLOTHING

FIELD OF THE INVENTION

The present invention generally relates to a retainer device to support loose wiring or tubing from articles of clothing and, more particularly, to a retention device that is detachably connectable to clothing to prevent electronic wiring or medical tubing from hanging loose from a person by detachably securing the wires or tubing to an article of clothing worn by the person utilizing the wiring or tubing.

BACKGROUND OF THE INVENTION

Patients in hospitals are often connected to an intravenous system to deliver medicines and saline solution to the patient. Often the tubing interconnecting the supply of medicine and/or saline solution and the patient is sufficiently long in order to providing some maneuverability for the patient that the tubing hangs well below the patient's arms when standing. This low hanging tubing presents a safety hazard in that the loop of tubing hanging at the lowest point is subjected to engaging protruding obstacles and can then pull on the patient's catheter or other connection with the patient. While the use of catheter tubing may be the most common situation in which tubing is hanging from a patient, other similar situations can be found on patients with medicinal pumps, patients with urinary catheters, and patients with feeding tubes, as a few examples.

Another remotely similar situation occurs with respect to electronic equipment. In the medical field, a patient can have electronic medical equipment with lead wires, such as EKG monitors and the like, or simply head phone wires, or ear bud wires, such as are connected to iPods to allow the wearer to hear audio programs as well as music stored in the electronic device. Often these electronic wires dangle from the wearer's ears to the location of the electronic device is attached to the wearer where electronic device is supported with a sufficient length to allow the wearer to have significant flexibility in locating the support place for the electronic device. As with the catheter tubing, the electronic wiring can be engaged by protruding obstacles that pull the hearing implements or medical monitors, etc., away from the wearer and/or the electronic device, thus interrupting the transmission of the desired electronic signal or simply the listening enjoyment of the wearer.

A solution to this problem of dangling catheter tubing, wires, etc., particularly when the patient is ambulatory, is often solved by the use of a safety pin that captures the tubing/wiring and is then pinned to the clothing worn by the patient, which is often a thin cotton, or similar material, hospital gown. While this use of a safety pin presents a perfunctory solution to the problem of the dangling catheter tubing, the safety pin cannot be used when the patient is being subjected to tests such as a an X-ray or an MRI, as the metal safety pin has to be removed to perform the tests due to the nature of the machine not being receptive to metal.

It would be desirable to provide a retention device that could engage medical tubing or electronic wiring to permit the tubing or wiring to be supported on an article of clothing of the wearer, which would prevent the loop of tubing from hanging too low or away from the wearer for engagement with a protruding obstacle. If allowed with respect to a machine on which testing is being done on the patient, the retention device may not have to be removed, thus retaining control of the tubing even while certain tests are being conducted.

SUMMARY OF THE INVENTION

It is an object of this invention to provide a device for securing loose tubing or wires to clothing in a temporary manner.

It is a feature of this invention that the device for securing loose tubing can be utilized to secure IV tubing for patients in hospitals.

It is an advantage of this invention that the secured tubing is less likely to be engaged with extraneous objects when the patient is walking from one location to another.

It is another feature of this invention that the device for securing tubing can also be utilized to secure electronic wiring to clothing while an electronic device is being operated.

It is another advantage of this invention that the device can secure wires for headphones or ear buds for an electronic device like an iPod® while the device is being used and the operator is moving.

It is another object of this invention to provide a device for securing tubing to clothing in which the device can be engaged to clothing and attached to the tubing to secure the tubing to the article of clothing selected.

It is still another feature of this invention that the device for securing tubing to clothing includes a primary body portion and a closure member that is engagable with the primary body portion to trap an article of clothing therebetween.

It is still another feature of this invention that the primary body portion is formed with at least two clips to receive tubing therein.

It is still another advantage of this invention that the tubing clips can be sized to fit tubing of different diameters, as well as electronic wiring.

It is yet another feature of this invention that the primary body portion is formed with a shaped opening that includes an enlarged generally circular end to permit the passage of the head of the button attached to the primary body portion by a tether, and a narrowed linear opening in communication with the enlarged circular end that enables the button to slide into a locking orientation trapping an article of clothing between the button and the primary body portion.

It is yet another advantage of this invention that the device can be formed of plastic through injection molding as a single integral device including both the primary body portion and the tethered closure button.

It is yet another object of this invention to provide a device for securing medical tubing or electronic wiring to an article of clothing, which is durable in construction, inexpensive of manufacture, carefree of maintenance, facile in assemblage, and simple and effective in use.

These and other objects, features and advantages are accomplished according to the instant invention by providing a device for securing tubing or wiring to an article of clothing in which the device is formed from plastic by injection molding or other suitable manufacturing process. The device includes a primary body portion that is formed with a shaped opening therein. The shaped opening has an enlarged circular part and an integral linear part. The device also includes a closure button formed with a narrow neck attached to a generally planar support member, which in turn is connected to the primary body portion by a tether. The button is sized to fit through the circular opening so that the neck can slide into the linear part and trap an article of clothing between the closure member and the primary body portion. The primary body portion is also formed with a pair of clips that are appropriately sized to receive tubing, such as IV tubing, that can be supported on the patient's clothing and facilitate mobility for the patient.

BRIEF DESCRIPTION OF THE DRAWINGS

The advantages of this invention will be apparent upon consideration of the following detailed disclosure of the invention, especially when taken in conjunction with the accompanying drawings wherein:

FIG. 1 is a top plan view of a tube holding device incorporating the principles of the instant invention;

FIG. 2 is a side elevational view of the tube holding device shown in FIG. 1;

FIG. 3 is a end elevational view of the tube holding device shown in FIG. 1;

FIG. 4 is a perspective view of the tube holding device shown in FIG. 1;

FIG. 12 is a top plan view of an alternative embodiment of the device incorporating the principles of the instant invention and being operable for supporting both IV and feed tubing;

FIG. 13 is an end elevational view of the device corresponding to lines 13-13 of FIG. 12;

FIG. 14 is a side elevational view of the device corresponding to lines 14-14 of FIG. 12; and FIG. 15 is a perspective view of the device depicted in FIG. 12.

DETAILED DESCRIPTION OF THE PREFERRED EMBODIMENT

Figure 5:
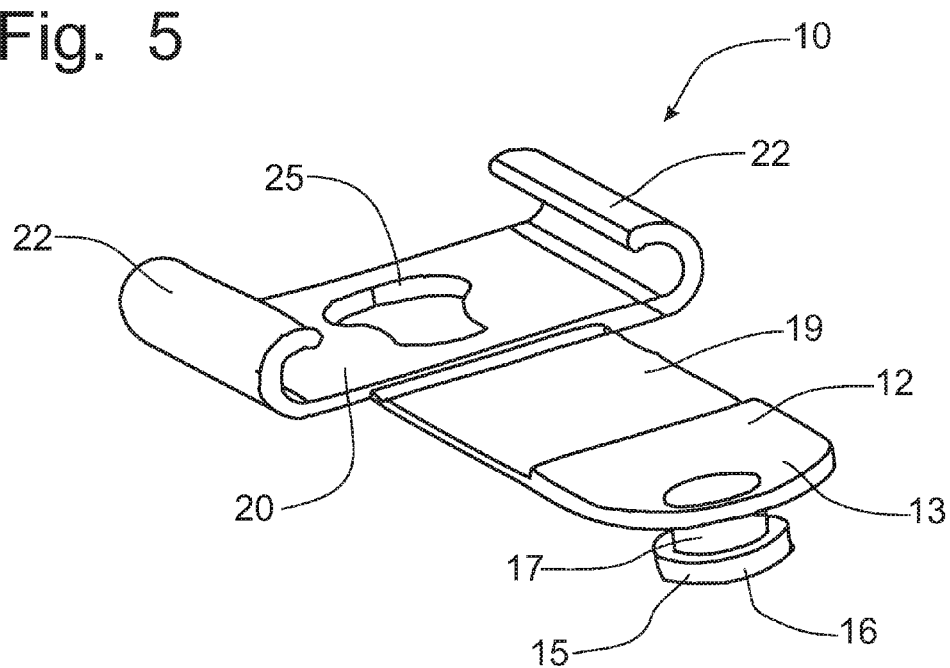
FIG. 5 is a perspective view of the tube holding device having a slightly different configuration than the tube holding device shown in FIG. 1.
Figure 6:
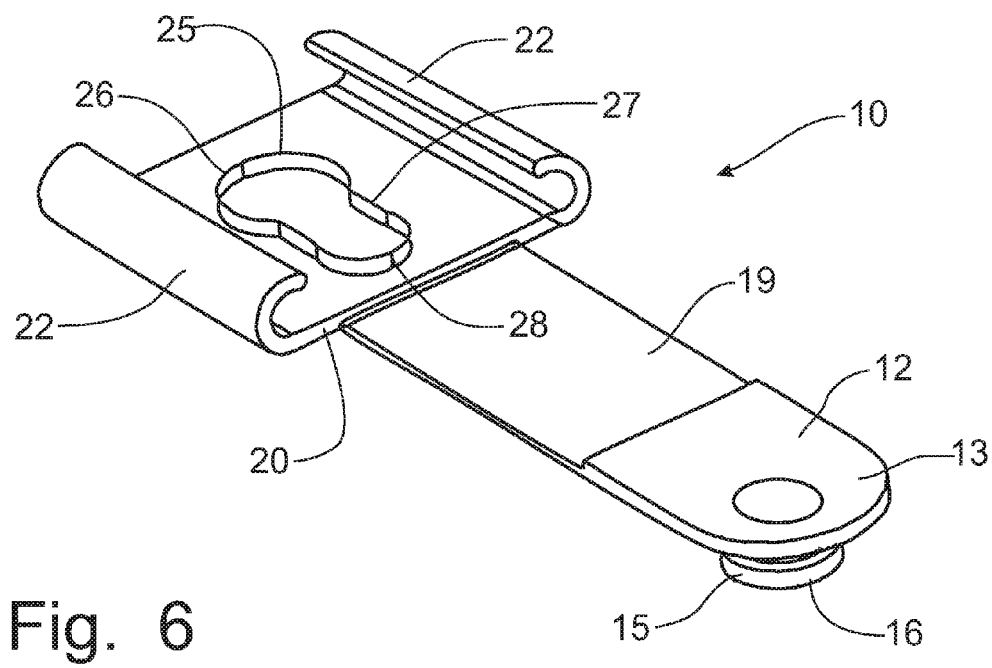
FIG. 6 is another perspective view of the tube holding device shown in FIG. 1.

Referring to FIGS. 1-4, a tube holding device incorporating the principles of the instant invention can best be seen. The tube holding device 10 is designed to support conventional medical tubing used for intravenous therapy for patients, catheters and other conventional tubing therapies and practices. As will be noted below, a slight reconfiguration of the primary body portion 20 with or without an inserted disc to engage electronic wires connecting medical monitoring or testing devices, as well as head phones or ear buds to electronic devices, such as iPods, will permit the tube holding device to support the electronic wires. Medical tubing, or in the alternative electronic wiring, is typically supplied in sufficient length to provide some flexibility in movement relative to the medical device, or in the alternative the electronic device, to which the medical tubing or electronic wiring is attached. This extra length of tubing or wiring hangs from one end connected to the medical or electronic device to the person using the medical or electronic device. Referring herein to medical tubing, the medical tubing will hang from the supply of medicine or fluid, or disposal bag, to the connection of that tubing to the patient. This length of medical tubing hangs in a loop that will extend far enough away from the body of the person using the tubing to engage a protruding obstacle and cause damage to the tubing or to the person.

The tube holding device 10 is formed with a primary body portion 20 and an attached closure member 12. One skilled in the art will recognize that the attachment of the closure member 12 to the primary body portion 20 is a matter of convenience and of preference. Although the closure member 12 would operate in the same manner as will be described in greater detail below if the closure member 12 were separate from the primary body portion 20, but when the two components are disengaged, there would be a tendency or probability of losing one of the two components. The tube holding device 10 is preferably formed from plastic through an injection molding process. Accordingly, the tether 19 connecting the closure member 12 to the primary body portion 20 can be of any size or shape; however, the preferred embodiment would be to have the tether 19 formed from a reduced thickness of plastic material so as to render the tether 19 flexible and enable the closure member 12 to be manipulated relative to the primary body portion 20.

The closure member 12 is preferably formed with a planar support member 13 having a button 15 projecting out of the bottom surface thereof. The button 15 is preferably shaped with an enlarged head 16 mounted at the end of a reduced shank 17. The tether 19 allows the closure member 12 to be folded back toward the primary body portion 20 in which configuration the button 15 becomes upright for engagement with the primary body portion 20, as will be described in greater detail below. Preferably, the planar support member 13 is formed to have a thickness greater than the tether 19 so that the planar support member 13 is not as flexible. In an alternative embodiment, the tether 19 could be formed to have a width much narrower than the planar support member 13; however, care must be taken that the tether 19 is not subject to being broken from repeated usage. Accordingly, it has been found that forming the tether 19 with a width substantially equal to the planar support member 13, though with a reduced thickness to induce increased flexibility, provides for a pleasing appearance and proper function.

The primary body portion 20 is also generally planar except that the lateral sides of the primary body portion 20 are formed into a specific curled shaped to form semi-circular clips 22 that are designed to mate with standard medical tubing 30. For catheter tubing, which has a larger diameter than IV tubing, the clips 22 would be formed with a larger diameter so as to conform to the size of the larger tubing. Conversely, if the primary body portion 20 is to be used to engage ear bud wiring for an iPod, as an example or other such electronic devices, the clips 22 should be formed at a smaller diameter so as to be engagable with the wiring for the same purposes to be described below with respect to the medical tubing 30.

Figure 7:
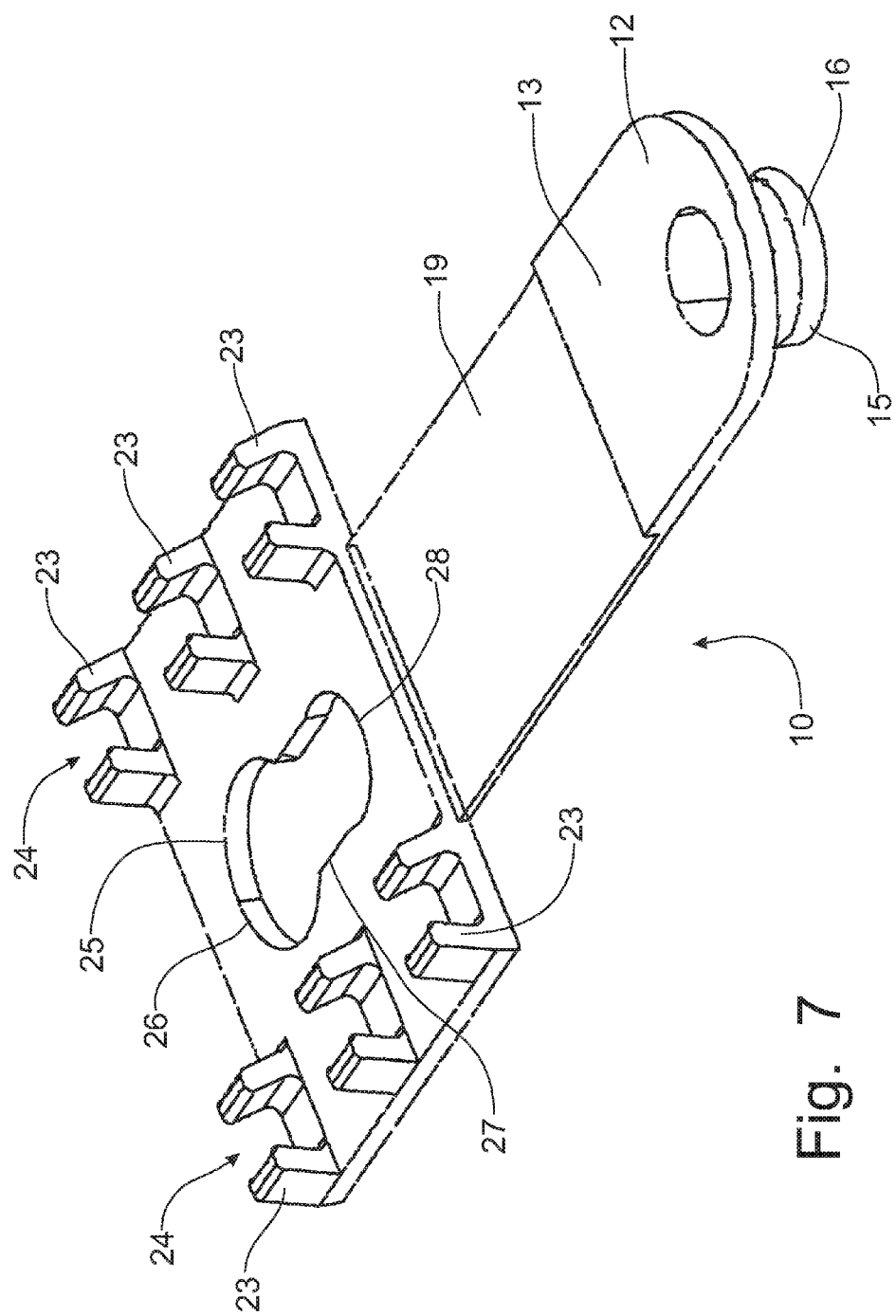
FIG. 7 is a perspective view of another embodiment of the tube holding device.
Figure 8:
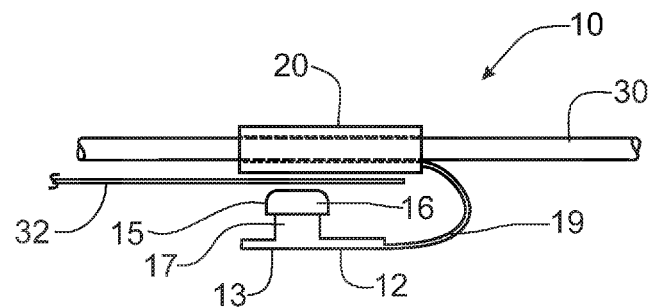
FIG. 8 is a side elevational view of the tube holding device shown in FIG. 1 with the closure member moved to be engaged with the primary body portion.
Figure 9:
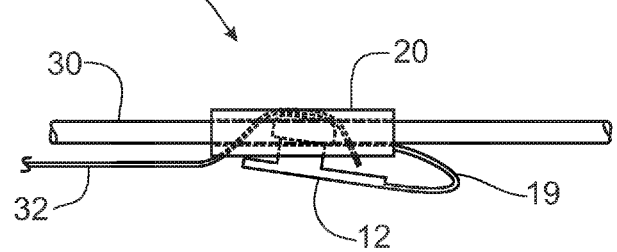
FIG. 9 is a side elevational view of the tube holding device shown in FIG. 8 with the closure member being inserted into the primary body portion to secure the tube holding device onto a representative piece of clothing.
Figure 10:
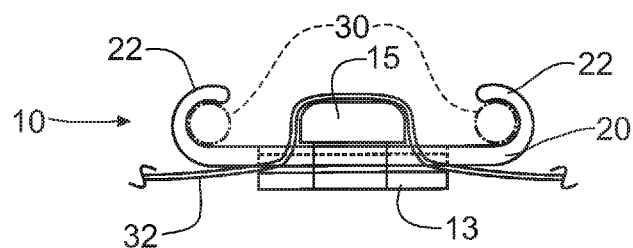
FIG. 10 is an enlarged end elevational view of the tube holding device as shown in FIG. 9.
Figure 11:
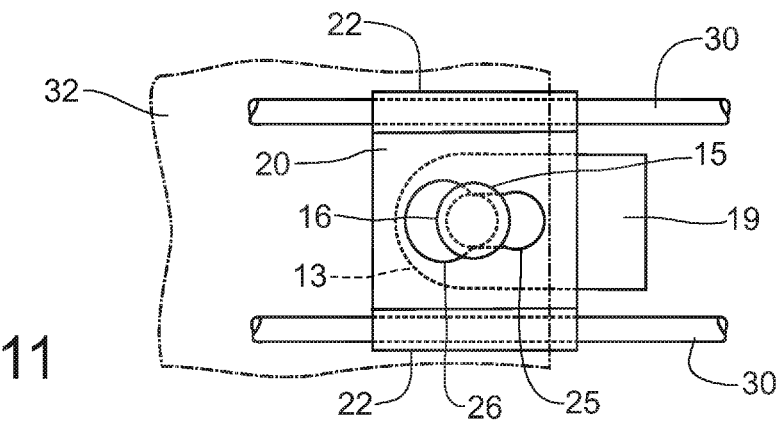
FIG. 11 is an enlarged top plan view of the tube holding device as shown in FIG. 9, the representative piece of clothing to which the tube holding device is secured being shown in phantom.

Between the two laterally opposed clips 22, the planar primary body portion 20 is formed with a shaped opening 25 that preferably has an enlarged generally circular end 26, which permits the passage of the head 16 of the button 15 through the primary body portion 20, and a narrowed linear opening 27 in communication with the enlarged circular end 26. The linear opening 27 has a width that will allow the passage of the reduced shank 17 of the button 15 along the length thereof. Optionally, the linear opening 17 can terminate in a reduced diameter circular opening 28 at the end thereof opposite the enlarged circular end 26 to mate with the circular shape of the shank 17. As another option, the reduced circular opening 28 could be slightly larger in width than the linear opening 27, as is represented in FIG. 7, to accommodate the securing of both the shank 17 and the thickness of material of clothing, as is described in greater detail below. Preferably, the tether 19 is connected to the primary body portion 20 adjacent the reduced circular opening 28 to facilitate the engagement of the button 15 into the shaped opening 25.

Referring to FIGS. 5 and 7, alternative embodiments of the tube holding device 10 can be seen. The primary difference of the tube holding device 10 in FIG. 5 is the width of the primary body portion 20 and the diameter of the clips 22 on the lateral sides of the primary body portion 20. The primary body portion 20 is wider than the configuration shown in FIGS. 1-4, so that the clips 22 can have a larger diameter to accommodate catheter tubing instead of intravenous medical tubing. By supporting the larger catheter tubing, the width of the primary body portion 20 would preferably be larger than the primary body portion 20 of the tube holding device 10 used with IV tubing so that there would be sufficient room to form the shaped opening 25 between the clips 22. In FIG. 7, the clips at the lateral sides of the primary body portion 20 are formed of at least two upright clip members 23 that are sized to receive the medical tubing through the vertically oriented openings 24 and be retained therein through a friction fit with the clip members 23. Accordingly, the tubing 30 is simply pressed into the clip members 23 and retained therein until pulled out of the clip members 23.

Referring now to FIGS. 8-11, the operation of the tube holding device 10 can best be seen. First, the medical tubing 30, or in the alternative electronic wiring or other hanging lines that require control, are placed into the clips 22 on the primary body portion 20. The curved clips 22 have a shape that will allow the tubing 30 to slide along the clips 22, or from the viewpoint of the tubing 30, the primary body portion 20 slides along the tubing 30, so that the tube holding device 10 can be positioned as desired along the length of the medical tubing 30 hanging loose from the person utilizing the tube holding device 10. Once the primary body portion 20 has been secured on the tubing 30, the closure member 12 is rotated toward the underside of the primary body portion 20. For those configurations in which the closure member 12 is not physically attached to the primary body portion 20, the closure member 12 is simply grasped an oriented below the underside of the primary body portion 20 with the button 15 projecting upwardly toward the shaped opening 25.

The closure member 12 and the primary body portion 20 are then oriented with respect to an article of clothing 32 being worn by the person utilizing the tube holding device 10 such that the material is positioned between the button 15 and the underside of the primary body portion 20. The button 15 is then pressed into the enlarged circular opening 26 taking the material of the article of clothing 32 with the button 15 until the head 16 and the material overlying the head 16 is pressed through the enlarged circular opening 26. The button 15 can then be move along the linear opening 27, with the material of the article of clothing 32 being caught between the shank 17 and the sides of the linear opening 27, until the button 15 is secured within the shaped opening 25, which due to the material of the article of clothing 32 trapped between the button 15 and the primary body portion 20 affixes the tube holding device 10 to the article of clothing 32.

As a result, the tube holding device 10 is secured to the article of clothing 32 which in turn secures the medical tubing 30 to the article of clothing. With appropriate location of the tube holding device 10 relative to the article of clothing 32, the medical tubing will be lifted onto the tube holding device 10 and will not be free to dangle away from the person using the medical tubing 30. Thus, a patient utilizing the tube holding device 10 to secure the medical tubing 30 to the article of clothing 32 (which is often a thin hospital gown) is less likely to engage a loop of the medical tubing 30 with a protruding object that will pull on the tubing. For tubing 30 that is so long as to present a danger of stepping on the loop of tubing while walking, the tube holding device 10 keeps the tubing elevated and secured to the article of clothing 32.

An alternative embodiment of the tube holding device 40 is depicted in FIGS. 12-15 in which the tube holding device 40 is formed to be able to connect with and support two different sizes of tubing, such as an IV tube 34 and a feed tube 36. The alternative tube holding device 40 has a rectangularly shaped body member 46 on which are mounted opposing grips for engaging tubing of different sizes. On one side of the body member 46 are a mounted two pairs of short IV tubing grips 47. In each pair of IV tubing grips 47, one of the grips 47a is generally upright while the opposing grip 47b is angled upwardly from the body member 46 and toward the upright grip 47a. This arrangement of the grips 47a, 47b forms an opening at the top of the grips 47a, 47b that is smaller than the opening between the grips 47a, 47b adjacent the body member 46, and presents a device that traps the IV tubing within the pair of grips 47. To get the tubing into engagement with the pair of grips 47, the angled grip 47b is tipped backward away from the upright grip 47a so that the tubing can pass between the grips 47a, 47b and be positioned adjacent the base member 46.

The opposite side of the body member 46 is formed with two pairs of larger grips 48 that are sized to receive feed tubing 36 which has a larger diameter than IV tubing 34. As described above, the feed tubing grips 48 include an upright grip 48a and an angled grip 48b that are arranged similarly to the IV tubing grips 47 and operate essentially identically. Accordingly, the alternative device 40 is operable to engage and support two different sizes of tubing 34, 36 simultaneously or individually, as the need dictates. Alternatively, the two grip members 47a, 47b or 48a, 48b, can both be angled upwardly from the base member 46 and toward the other grip member of the pair 47, 48, as is depicted in FIG. 13.

Like the first embodiment described above, the alternative embodiment includes a tether 41 that interconnects a closure member 42 to the body member 46. The closure member 42 incorporates a button 43 that is sized and shaped to pass through the shaped opening 45 to capture a section of clothing material of the patient in order to support the tubing engaged with the respective grips 47, 48, as noted and described noted above. The tether 41 can incorporate a ridge 44 at the joinder of the closure member 42 to the tether 41. The ridge 44 facilitates the positioning of the button 43 within the shaped opening 45, particularly when a section of clothing is positioned between the button 43 and the shaped opening 45. Also, the body member 46 is formed with slots 49 on the opposing sides of the shaped opening 45 to provide the ability to wrap small electronic wires, such as heart monitor wires or ear bud wires, around the body member 46.

One skilled in the art will also note that the alternative embodiment of the tube holding device 40 can be formed with pairs of grips 47, 48 that are sized to engage electronic cords as well as different kinds of medical tubing, such as IV tubing, feeding tubing, oxygen tubing, catheters, chest tubes and heart tubes. Accordingly, the tube holding device 10, 40 can be utilized with electronic devices (not shown) having loose cords that can be controlled through the utilization of the tube holding device 10, 40. In addition, the tether 19, 41 can be wrapped around an object to secure electronic cords or cables (not shown) to the object while the button 15, 43 is engaged into the shaped opening 25, 45. One skilled in the art will also recognize that the tube holding device 10, 40, particularly the alternative configuration 40, can be formed with multiple pairs of grips or clips to hold more than two tubes, cords or cables.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiments of the invention; however, concepts, as based upon the description, may be employed in other embodiments without departing from the scope of the invention.

As an example, one skilled in the art will recognize that the closure member 12 could be selectively separable from the primary body portion 20 when engaged or not engaged therewith. In such a configuration, the closure member 12 could have a tether that is selectively detachable from the main body portion 20 so as to be removable therefrom under conditions where the tube holding device 10 needs to be secured to the article of clothing at a location that is not proximate to an edge of the article of clothing. Such a structure could loop (not shown) on the body portion 20 that would receive a hook or transverse member (not shown) on the tether and retain the tether within the loop until the transverse member was manually manipulated to release the transverse member from the loop. In such a configuration, the tube holding device 10 could be utilized in the same manner as described above, or as a detached closure member 12.

Having thus described the invention, what is claimed is:

1. A device for securing tubing or wiring to an article of clothing comprising:
   a primary body portion including a pair of clip retention members mounted on opposing sides of said primary body portion for retaining tubing therein, and a shaped opening including a linear portion, said shaped opening being located between said pair of clip retention members; and
   a closure member including a button having a first size dimension mounted on a neck having a second size dimension, said second size dimension being smaller than said first size dimension, said button being engagable with said shaped opening while said neck permits said button to move along said linear portion.

2. The device of claim 1 wherein said neck is attached to a mounting member connected to said primary body portion by a tether, said tether permitting said mounting member to be moved relative to said primary body portion to align said button with said shaped opening.

3. The device of claim 2 wherein said tether and said mounting member have a common width dimension, said common width dimension being less than a corresponding width dimension of said primary body portion.

4. The device of claim 1 wherein said shaped opening includes a circular portion with said linear portion being in communication with said circular portion such that said button can be passed through said circular portion and moved to said linear portion.

5. The device of claim 1 wherein said clip retention members are formed as semi-circular members curled upwardly from said primary body portion to provide an opening between edges of said semi-circular members and said primary body portion for the passage of tubing or wiring into the respective said clip retention member.

6. The device of claim 1 wherein said clip retention members are formed as upright members defining a vertically oriented opening for the passage of tubing or wiring into the upright members.

7. The device of claim 1 wherein said clip retention members have a diameter sized to correspond to a predetermined size of medical tubing.

8. The device of claim 1 wherein said clip retention members have different diameters to receive differently sized tubing or wiring.

9. A method of securing tubing or wiring to clothing, comprising:
   providing a plastic device having a primary body portion including at least one clip retention member for retaining said tubing or wiring therein, and a shaped opening including a linear portion; and a closure member including a button having a first size dimension mounted on a neck having a second size dimension, said second size dimension being smaller than said first size dimension, said neck being attached to a mounting member connected to said primary body portion by a tether, said tether permitting said mounting member to be moved relative to said primary body portion to align said button with said shaped opening;
   placing said clothing underneath said primary body portion;
   moving said button to a position underneath said primary body portion and said clothing;
   pushing said button through said shaped opening and force said clothing through said shaped opening;
   sliding said neck into said linear portion of said shaped opening to trap said clothing between said neck and said primary body portion; and
   connecting said tubing or wiring to said at least one clip retention member.

10. The method of claim 9 wherein said plastic device secures medical tubing to said at least one clip retention member.

11. The method of claim 10 wherein said shaped opening includes a circular portion with said linear portion being in communication with said circular portion, said button being circular in shape.

12. The method of claim 10 wherein said primary body portion has a pair of clip retention members for retaining tubing or wiring with said clip retention members being mounted on opposing sides of said primary body portion, said connecting step connecting medical tubing to each said clip.

13. The method of claim 12 wherein said clip retention members are formed as semi-circular members curled upwardly from said primary body portion to provide an opening between an edge of said semi-circular member and said primary body portion for the passage of tubing into said clip retention member, said connecting step including the step of sliding said medical tubing through said opening to be trapped within said semi-circular member.

14. The method of claim 12 wherein said clip retention members are formed as upright members defining a vertically oriented opening for the passage of tubing into the upright members, said connecting step including the step of pressing said medical tubing through respective said vertically oriented openings to trap said medical tubing in said upright members.

15. The method of claim 12 wherein said medical tubing is one of IV tubing, oxygen tubing, catheter tubing, chest drainage tubing, and heart tubing.

16. A device for securing medical tubing to an article of clothing worn by a patient, comprising:
   a plastic primary body portion including a pair of retainer clips for selectively retaining said medical tubing therein, said primary body portion further including a shaped opening therein located between said retainer clips, said shaped opening having a circular portion and a linear portion in communication with said circular portion; and
   a plastic closure member including a mounting member connected to said primary body portion by a tether, said mounting member having an integral circular button spaced above said mounting member by a neck, said button having a first diameter dimension that is larger than a corresponding diameter dimension of said neck, said tether permitting said mounting member to be moved relative to said primary body portion to align said button with said shaped opening.

17. The device of claim 16 wherein said retainer clips are formed as integral semi-circular members curled upwardly from said primary body portion to provide an opening between edges of said semi-circular members and said primary body portion for the passage of said medical tubing into the respective said retainer clip.

18. The device of claim 16 wherein said retainer clips are formed as upright members defining a vertically oriented opening for the passage of medical tubing into the upright members.

19. The device of claim 16 wherein said retainer clips are sized to receive one of IV tubing, oxygen tubing, catheter tubing, chest drainage tubing, and heart tubing.

* * * * *